(12) United States Patent
Cappione, III et al.

(10) Patent No.: US 10,140,419 B2
(45) Date of Patent: Nov. 27, 2018

(54) GRAPHICAL USER INTERFACE FOR ANALYSIS AND COMPARISON OF LOCATION-SPECIFIC MULTIPARAMETER DATA SETS

(71) Applicant: EMD Millipore Corporation, Burlington, MA (US)

(72) Inventors: Amedeo Joseph Cappione, III, San Francisco, CA (US); Ray Lefebvre, Berkeley, CA (US); Neil Kilcoin, Pleasant Hill, CA (US); David Andrew King, Menlo Park, CA (US); George J. Dixon, Socorro, NM (US)

(73) Assignee: EMD Millipore Corporation, Burlington, MA (US)

( * ) Notice: Subject to any disclaimer, the term of this patent is extended or adjusted under 35 U.S.C. 154(b) by 458 days.

(21) Appl. No.: 14/598,878

(22) Filed: Jan. 16, 2015

(65) Prior Publication Data

US 2015/0135119 A1 May 14, 2015

Related U.S. Application Data

(63) Continuation of application No. 12/104,234, filed on Apr. 16, 2008, now Pat. No. 8,959,448.

(Continued)

(51) Int. Cl.
*G06F 19/26* (2011.01)
*G01N 35/00* (2006.01)
(Continued)

(52) U.S. Cl.
CPC ....... *G06F 19/26* (2013.01); *G01N 35/00722* (2013.01); *G06F 3/04817* (2013.01);
(Continued)

(58) Field of Classification Search
CPC . G06F 3/048; G06F 19/00; G06F 8/10; G06F 19/26; G06F 3/0487;
(Continued)

(56) References Cited

U.S. PATENT DOCUMENTS 4,845,653 A 7/1989 Conrad et al.
5,644,692 A 7/1997 Eick
(Continued)

FOREIGN PATENT DOCUMENTS

| JP | 2006-90734 A | 5/2006 |
|---|---|---|
| WO | 01/65349 A1 | 9/2001 |
| WO | 02/056026 A1 | 7/2002 |

OTHER PUBLICATIONS

"BD CellQuest Pro Software User's Guide", Part No. 349226 Rev A., Jul. 2002, (258 pages).
(Continued)

*Primary Examiner* — Sherrod L Keaton
(74) *Attorney, Agent, or Firm* — EMD Millipore Corporation

(57) ABSTRACT

A graphical user interface on a computer provides for the analysis of location specific data and the presentation of analysis results for visual comparison by a user. Results of the analysis are visually presented as icons subdivided into regions and arranged in such a way that the user is able to associate each icon with a data location. A visual presentation of results in the icons and regions allows a user to visually compare the analysis results in two or more data sets according to location. The graphical user interface further provides for the definition and adjustment of an analysis through the interaction of a user with a graphical representation of the analysis. In some cases, the visual presentation of results tracks the analysis adjustments so the user can visually observe the effects that the adjustments have on the results. A method of interacting with the interface to define (Continued)

an analysis and represent results and a method of presenting two or more data sets using the interface are described. The interface can be used to analyze and visually compare the results of location specific data from a number of sources and is illustrated in a flow cytometry application.

7 Claims, 18 Drawing Sheets

Related U.S. Application Data

(60) Provisional application No. 60/912,361, filed on Apr. 17, 2007.

(51) Int. Cl.
G06F 3/0481 (2013.01)
G01N 15/14 (2006.01)

(52) U.S. Cl.
CPC .......... G01N 2015/1402 (2013.01); G01N 2015/1477 (2013.01); G01N 2035/0091 (2013.01)

(58) Field of Classification Search
CPC .......... G05B 2219/23258; G05B 2219/35488; A61B 5/0059; A61B 5/743; A61B 5/735; G06T 19/00; G06T 2200/24; G06T 7/0012; G01N 2015/1402; G01N 35/00722
See application file for complete search history.

(56) References Cited

U.S. PATENT DOCUMENTS

| | | | |
|---|---|---|---|
| 5,742,777 A | 4/1998 | Eick | |
| 5,825,357 A | 10/1998 | Malamud et al. | |
| 5,894,311 A | 4/1999 | Jackson | |
| 5,989,835 A | 11/1999 | Dunlay et al. | |
| 6,178,382 B1 | 1/2001 | Roederer et al. | |
| 6,384,847 B1 | 5/2002 | Rabenhorst | |
| 6,519,355 B2* | 2/2003 | Nelson | G01N 15/147 382/133 |
| 6,631,211 B1 | 10/2003 | Schermer et al. | |
| 6,821,787 B2* | 11/2004 | Neilson | G01N 25/482 422/82.05 |
| 6,909,981 B2* | 6/2005 | Gavin | H01J 49/0036 250/340 |
| 7,343,305 B2 | 3/2008 | Benn et al. | |
| 2001/0050999 A1* | 12/2001 | Bacus | G01N 15/1475 382/128 |
| 2002/0098593 A1 | 7/2002 | Nelson et al. | |
| 2002/0120602 A1* | 8/2002 | Overbeek | G06F 19/28 |
| 2003/0030637 A1 | 2/2003 | Grinstein et al. | |
| 2003/0044843 A1 | 3/2003 | Tanaka et al. | |
| 2003/0095135 A1 | 5/2003 | Kaasila et al. | |
| 2004/0033610 A1* | 2/2004 | Lovell | B01L 3/5085 436/43 |
| 2004/0241730 A1 | 12/2004 | Yakhini et al. | |
| 2005/0002552 A1 | 1/2005 | Dunn et al. | |
| 2005/0148040 A1* | 7/2005 | Thadhani | G01N 33/689 435/7.92 |
| 2006/0020398 A1 | 1/2006 | Vernon et al. | |
| 2006/0179032 A1 | 8/2006 | Gottsman | |
| 2008/0228444 A1 | 9/2008 | Olson et al. | |
| 2008/0241820 A1* | 10/2008 | Krutzik | G01N 33/537 435/5 |

OTHER PUBLICATIONS

"BD FACSCalibur System", BD FACSCailbur System retrieved from http://www.bdbiosciences.com/features/products/display—product.php?keyID=45 on Aug. 5, 2008 (2 pages).

"Bioinformatics: Bringing it all Together"; Nature, vol. 419; Oct. 17, 2002; (pp. 751-757).
"Data Management Software", retrieved from http://www.bdbiosciences.com/features/products/display—product.php? keyID=46 on Aug. 5, 2008 (4 pages).
"EasyCyte Plus System", Guava Technologies, retrieved from http://guavatechnologies.com/cm/Life%20Science%20Research/Platform.EasyCyte%20PI on Aug. 5, 2008 (1 page).
"FCS Express Version 3 Manual" Copyright De Novo Software, 2001-2008, (200 pages).
"iColor™ Fluoro-Chromatic Imaging Cytometer", retrieved from http://www.compucyte.com/icolor.htm on Aug. 5, 2008 (1 page).
"ISAC—Data File Standard Flow Cytometry, Version FCS3.0"; retrieved from http://www.isac-net.org/index.php?option=com—content&task=view&id=101&Itemid=46 ; Dec. 10, 2007 (24 pages).
"MiraiBio a Division of Hitachi Software, Tutorial for MasterPlex GT v2"; Hitachi Software Engineering America, Ltd. 2006 (pp. 1-22).
"Overview", FLOWJO web page http://www.flowjo.com/v7/html/overview.html retrieved on Aug. 5, 2008 (5 pages).
"PCA-96 System", retrieved from http://guavatechnologies.com/cm/Life%20Science%20Research/Platforms/Personal%20Cel on Aug. 5, 2008.
BD Biosciences; "BD FACSCalibur Flow Cytometer" Jun. 2002 (11 pages).
Boguski, et al.; "Biomedical Informatics for Proteomics"; Nature; vol. 422; Mar. 13, 2003; (pp. 233-237).
Brazma; "Editorial on the Importance of Standardisation in Life Sciences"; Oxford University Press, vol. 17, No. 2; 2001 (pp. 113-114).
Compucyte; "iColor Fluro-Chromatic Imaging Cytometer" 2006 (2 pages).
Darzynkiewicz et al.; "Laser-Scanning Cytometry: A New Instrumentation with Many Applications"; Experimental Cell Research vol. 249; 1999 (pp. 1-12).
De Rosa, Stephen C., et al., "Beyond Six Colors: A new era in Flow Cytometry", Perspective, Nature Medicine, vol. 9, No. 1., Jan. 2003, pp. 112-117.
Edwards et al.; Flow Cytometry for High-Throughput, High-Content Screening; Current Opinion in Chemical Biology; 2004;8:392-398.
Eschrich et al.; "DNA Microarrays and Data Analysis: An Overview"; Surgery, Sep. 2004; (pp. 500-503I).
FCS Express, De Novo Software retrieved from http://www.denovosoftware.com/site/FCSExpress.shtml on Aug. 5, 2008 (1 page).
FLOWJO Manual, Flow Cytometry Analysis Software, Tree-Star, Inc. 1997-2007, (229 pages).
Guava Technologies; "Guava EasyCyte™ Plus System User's Guide"; Sep. 4, 2007; (330 pages).
Guava Technologies; "Guava PCA—96 System User's Guide" The Power of On-Demand Single Cell Analysis; Nov. 21, 2006; (242 pages).
Herzenber, Leonore A., et al., "Interpreting Flow Cytometry Data: A Guide for the Perplexed", Commentary, Nature Immunology, vol. 7, No. 7, Jul. 2002, pp. 681-685.
Krutzik et al.; "Fluorescent Cell Barcoding in Flow Cytometry Allows High-Throughput Drug Screening and Signaling Profiling"; Nature Methods, vol. 3 No. 5; May 2006; (pp. 361-368 pages).
Perfetto, Stephen P., et al., Seventeen-Colour Flow Cytometry: Unravelling the Immune System:, Perspective, Nature Reviews/Immunology, vol. 4., Aug. 2005, pp. 648-655.
Taylor; "Improving the Quality of HCS Assays with Optimized System S/N, Multiplexing, Statistics, Informatics and Systems Cell Biology"; Presentation—Cellument Inc.; 2005 (17 pages).
European Patent Office, Supplementary European Search Report in European Application No. 08746006, dated Oct. 16, 2017, 8 pages.
Indian Patent Office, Office Action in Indian Application No. 6742/CHENP/2009, dated Sep. 1, 2017, 6 pages.

* cited by examiner

FIGURE 11

PLATE 1 (224)

|   | 1 | 2 | 3 | 4 | 5 | 6 | 7 | 8 | 9 | 10 | 11 | 12 |
|---|---|---|---|---|---|---|---|---|---|----|----|----|
| A | ○ | ○ |   |   |   |   |   | ○ |   |    | ○  |    |
| B | ○ |   |   | ○ |   |   |   |   |   |    | ○  |    |
| C |   | ○ |   | ○ |   |   |   | ○ |   |    | ○  |    |
| D | ○ | ○ |   | ○ |   |   |   |   |   |    | ○  |    |
| E |   |   |   | ○ |   |   |   | ○ |   |    | ○  |    |
| F | ○ | ○ |   | ○ |   |   |   | ○ |   |    | ○  |    |
| G | ○ | ○ |   |   |   |   |   |   |   |    | ○  |    |
| H | ○ | ○ |   | ○ |   |   |   | ○ |   |    | ○  |    |

PLATE 2 (226)

|   | 1 | 2 | 3 | 4 | 5 | 6 | 7 | 8 | 9 | 10 | 11 | 12 |
|---|---|---|---|---|---|---|---|---|---|----|----|----|
| A |   | ○ |   |   |   |   | ○ |   | ○ | ○  |    |    |
| B |   | ○ |   | ○ |   |   | ○ |   |   | ○  |    |    |
| C |   | ○ |   | ○ |   |   |   |   | ○ | ○  |    |    |
| D |   | ○ |   | ○ |   |   | ○ |   |   | ○  |    |    |
| E |   | ○ |   |   |   |   | ○ |   | ○ | ○  |    |    |
| F |   | ○ |   | ○ |   |   |   |   | ○ | ○  |    |    |
| G |   | ○ |   | ○ |   |   | ○ |   | ○ |    |    |    |
| H |   | ○ |   |   |   |   | ○ |   | ○ | ○  |    |    |

GRAPHICAL USER INTERFACE FOR ANALYSIS AND COMPARISON OF LOCATION-SPECIFIC MULTIPARAMETER DATA SETS

CROSS REFERENCE TO RELATED APPLICATION

This application is a continuation of U.S. application Ser. No. 12/104,234 filed on Apr. 16, 2008, which claims priority to U.S. Provisional Patent Application 60/912,361, "Visual Analysis of Multiparameter Flow Cytometer Data," filed on Apr. 17, 2007, and the disclosures of all of which are incorporated herein by reference in their entirety.

TECHNICAL FIELD

The present invention relates generally to analyzing, displaying, and visually comparing location-specific, multi-parameter data sets and, more specifically, to analyzing, displaying and visually comparing data sets resulting from the cytometric interrogation of biological samples.

BACKGROUND

Incorporating recent advances in digital computer and numerical control techniques, analytical instruments are being designed to automatically interrogate a number of samples and measure two or more parameters during an interrogation. In typical measurement scenario, samples are positioned in locations on a carrier and the carrier is loaded into an instrument that automatically interrogates the locations. The gathered data may accurately be referred to as location-specific data since each of the interrogated samples is positioned in a known location on the sample carrier. Location-specific data may also be generated by an array of instruments, each of which is positioned in a known spatial relationship to the others.

Modern cytometers are representative of instruments that are designed to automatically analyze a number of samples on a carrier. These devices commonly interrogate particle-containing samples by illuminating the particles with one or more excitation light beams and detecting the colored light pulses that are generated by the particle-beam interaction. Flow cytometers focus the excitation light to define at least one excitation volume in a flow tube and the particles are transported through the focused light by a fluid flowing through the tube. Particles in a scanning cytometer are essentially stationary and the focused excitation light is scanned across the particles. In both classes of instrument, multicolored excitation beams may be formed by combining beams with different wavelengths. Information about the particles is provided by the wavelength, amplitude and shape of the colored light pulses.

Cytometers may be used to interrogate particle-containing biological samples containing molecules that are derived from living organisms. The particles in such samples may be surrounded by a solid, liquid or gaseous medium and often have fluorescent materials affixed to them to facilitate their interrogation. Commercial flow cytometers include capillary flow instruments such as the EasyCyte-Plus and PCA-96 manufactured by Guava Technologies of Hayward, Calif. and conventional sheath flow instruments such as the FAC-SCalibur manufactured by BD Biosciences of San Jose, Calif. The iColor Imaging Cytometer manufactured by Compucyte of Cambridge, Mass. is a representative scanning cytometer.

Advanced applications require cytometers with a large number of detectors as described in "Seventeen-colour Flow Cytometry: Unraveling the Immune System," by S. P. Perfetto, et al., *Nature Review Immunology*, vol. 4, pp. 649-655 (2004) and "Beyond Six Colors, a New Era in Flow Cytometry," S. C. DeRosa, et al., *Nature Medicine*, vol. 9, pp. 112-117 (2003). U.S. Pat. No. 6,683,357 issued to Clifford A. Oostman et al. on Jan. 27, 2004 describes a representative multiple laser cytometer system with a reflective filter system for advanced applications. Embodiments of the Oostman patent may have three or more excitation volumes and more than a dozen detectors.

Due to its complexity, the data generated by the interrogation of one of more samples with a cytometer are typically analyzed using a digital computer. Commercial software packages for cytometry data analysis include FCS Express from DeNovo Software, Los Angeles, Calif., FlowJO from the Stanford Shared FCS facility and licensed through Stanford University, Stanford, Calif. and CellQuest PRO from BD Biosciences, San Jose, Calif. Techniques for cytometry data analysis are also disclosed in U.S. Pat. No. 6,178,382 issued to Mario Roederer, et. al. on Jan. 23, 2001 and "Interpreting flow cytometry data: a guide for the perplexed," L. Herzenberg et al, *Nature Immunology*, Volume 7, pp. 681-685, July 2006.

SUMMARY

The present invention is directed to presenting output data to a user so as to enable visual comparison of two or more output data sets. The invention is further directed to interacting with a graphical interface that provides for such a comparison.

In accordance with one embodiment of the invention, a graphical user interface (GUI) for a computer system visually represents data of two or more output data sets in the context of a multiplexed, location-specific heat map. The heat map comprises icons representing a group of sample locations that have been interrogated to obtain location-specific input data, which is analyzed to generate the output data sets. The spatial arrangement of the icons in the map is visually similar to the physical arrangement of the samples so that each icon is visually associated with at least one sample location.

Furthermore, at least one of the icons is divided into regions so that data from different data sets may be visually represented in different regions and compared. In certain embodiments, the shape of the icons may be substantially the same as the shape of the sample locations, all of the icons may be divided into regions, or the arrangement of the samples and icons may be the same. In other embodiments, the output data sets may comprise data from two or more samples and the number of regions may be equal to the number of analyzed data sets. Data sets may be assigned to regions of the icons by the user and data values represented by visual tone or color. The numerical resolution of the tone or color representations may be further enhanced by superimposing a hatched pattern on the tone or color or by using the tone or color to represent the logarithm of the represented quantity. The data sets may result from the interrogation of particle-containing biological samples with a flow cytometer or a scanning cytometer.

In an alternative embodiment, a graphical user interface displays a representation of the analyses of data sets resulting from interrogating samples in an arrangement of samples and also displays a representation of the results of the analyses. This embodiment comprises a gate or alternative graphical representation of at least one analysis that is applied to a data set to generate results. The analysis has at least one parameter that a user controls by interacting with the graphical presentation and the results of the analysis are presented with at least one additional set of results using a multiplexed location-specific heat map. Variations in the results that are associated with changes in the parameter are visually represented in the heat map. Optionally, the parameter may be selected from a menu or be adjusted by changing the shape of a one, two, or three-dimensional figure in a graph. The visual representation of the analysis results may also track the changes in the analysis parameter, thereby allowing the user to observe the changes in output data associated with changes in the parameter. The input data analyzed and presented in the heat map may result from the interrogation of particle-containing biological samples with a flow or scanning cytometer.

Another aspect of the invention concerns interacting with the graphical interface. A user interacts with the interface by defining at least one analysis, specifying units of measurement for the analysis, applying the analysis to a data set to generate results and representing the results in a region of the icons. This method may be applied to analyzing and displaying results of the analysis of data that is generated by interrogating particle containing biological samples with a flow or scanning cytometer.

The invention is also embodied in the presentation of two or more data sets on a computer display for visual comparison by a user in which the data sets result from the analysis of an interrogation of an arrangement of samples. The presentation comprises mapping the arrangement of samples with visual icons in the display so that each icon is associated with at least one sample and the spatial relationship of each visual icon to the other icons is similar to the spatial relationship of the sample associated with the visual icon to the other samples, subdividing the icons into regions, and visually representing each data set in a unique region of the icons. This presentation may be used to present data resulting from the interrogation of particle containing biological samples with a flow or scanning cytometer.

BRIEF DESCRIPTION OF THE DRAWINGS

While the appended claims set forth the features of the present invention with particularity, the invention, together with its objects and advantages, may be best understood from the following detailed description taken in conjunction with the accompanying drawings of which:

FIG. 11 illustrates arrangements of samples in the wells of two 96-well sample plates.

DETAILED DESCRIPTION OF THE INVENTION

Features of the present invention are illustrated herein in the context of an application in which multiple samples are interrogated by a flow cytometer. This application of the invention is intended to be representative and not limiting. Alternative embodiments of the invention may be used for the display and comparison of analysis results from a wide range of interrogations other than flow cytometry.

Figure 1:
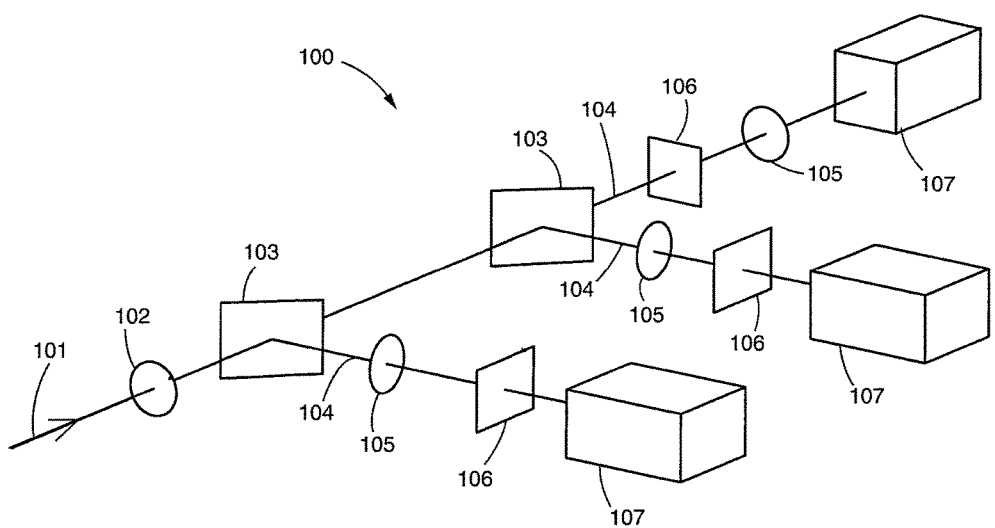
FIG. 1 shows a optical system for collecting, dividing and detecting light in a cytometer.

In a flow cytometer, the light from a sample is collected, separated according to wavelength and imaged onto detectors using an optical system, 100, similar to that shown in FIG. 1. Light 101, which is typically emitted by the sample in the form of pulses, is collected by a lens 102 and directed to dichroic beamsplitters 103 that divide the light 101 according to wavelength. The divided portions of the light travel along detection paths 104 that contain a focusing lens 105, a bandpass filter 106 and a detector 107. The detectors 107 convert the light to electronic signals that are transported via conventional means to an electronic processing unit (not shown).

In a typical system, the electronic signals are analog pulse trains and the electronic processing unit creates digital representations of the pulse trains generated by the detectors. The digital representations are commonly stored according to a defined format on a data transfer device. The File Cytometry Standard or FCS format developed by the Standards Committee of the International Society for Analytical Cytometery (ISAC) is one of many data storage formats that are suitable for file transfer.

The act of interrogating and recording light pulses from a single particle may be referred to as an event and the interrogation of similar particles generate pulses with a limited range of amplitudes in a subset of the detectors. In a cytometer with N detectors, the amplitudes of the pulses generated by all of the detectors during an event may be represented by an N-dimensional vector or a point in an N-dimensional data space. In the data space representation, input data is analyzed by counting the number of events that have point-representations within an M-dimensional (M less than or equal to N) volume. The projection of an M-dimensional volume onto a graph having one, two or three dimensions is commonly referred to as a "gate."

In an instrument with a single excitation source such as the EasyCyte Plus manufactured by Guava Technologies of Hayward, Calif., an event may generate output pulses from four to six different detectors. These detectors typically measure light pulses produced by forward scatter, large angle scatter and fluorescent emission at different wavelengths.

Figure 2:
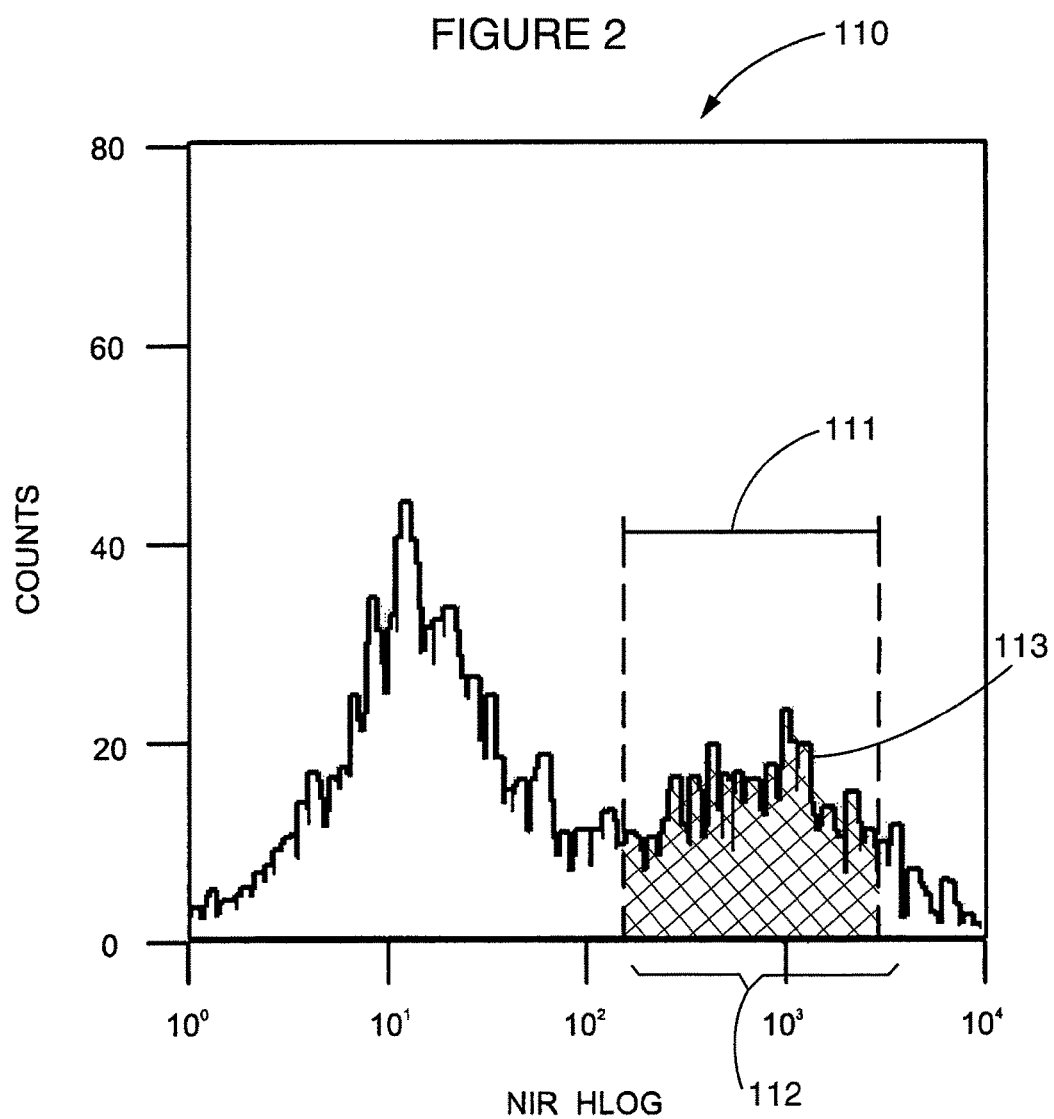
FIG. 2 shows a gated histogram used in the analysis of a cytometry data set.

In cases where particles of a specific type can be identified using pulses from a single detector, gates are commonly defined using a simple histogram 110 as illustrated in FIG. 2. In the histogram 110, the one-dimensional gate 111 corresponds to a range of abscissas 112 and the number of events falling inside the gate is equal to the area 113 under the portion of the histogram corresponding to the range of abscissas 112.

Figure 3:
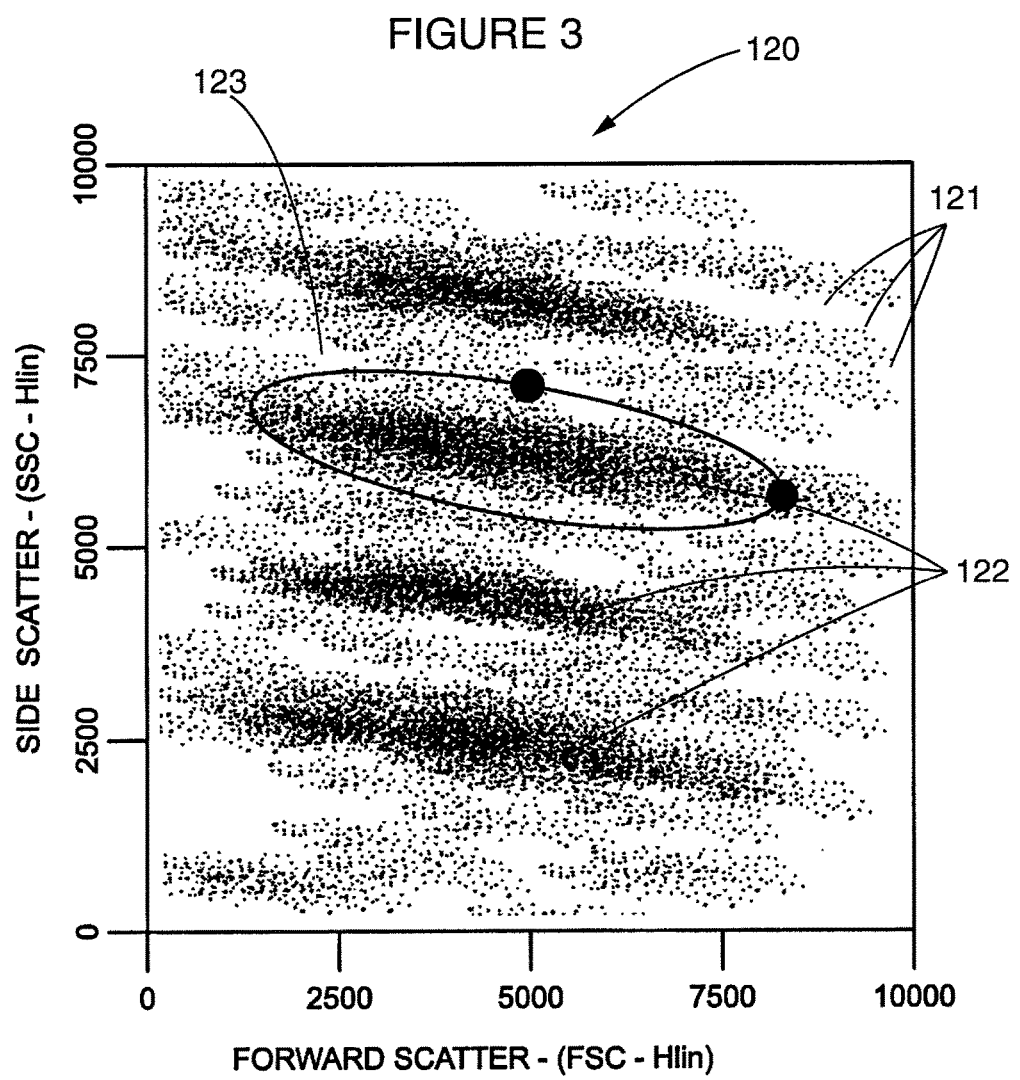
FIG. 3 shows a gated dot plot used in the analysis of a cytometry data set.

In cases where data from two detectors is required for particle identification, the data may be displayed as a dot plot in which the pulse amplitudes are shown on two orthogonal axes. A typical dot plot 120 is illustrated in FIG. 3. In the plot 120, pulse amplitudes from each event are plotted as points 121. Events resulting from the illumination of similar particles typically form clusters 122 of points 121 in on the dot plot. A gate is represented as a closed FIG. 123 on the dot plot and the size, shape and position of the FIG. 123 are optimized to separate points produced by particles with specific characteristics. The number of events caused by particles having the desired characteristics is determined by counting the points in the gate representation.

Modern cytometric measurements typically require volumes to be defined in data spaces having three or more dimensions. For example, a comparatively simple flow cytometer, the EasyCyte Plus manufactured by Guava Technologies of Hayward, Calif., has six detectors (four fluorescent and two scatter). In this device, a single event may generate a pulse in each detector and data analysis is typically carried out in a space with four to six coordinates. Visual representation of such a space is difficult and, consequently, commercial software packages for the analysis of flow cytometry data define volumes using logical combinations (AND, OR, NOT, etc.) of one and two dimensional gates. Gates may also be defined by projecting events onto three-dimensional cloud plots, two dimensional histograms, or through the use of various experimental techniques.

Figure 4:
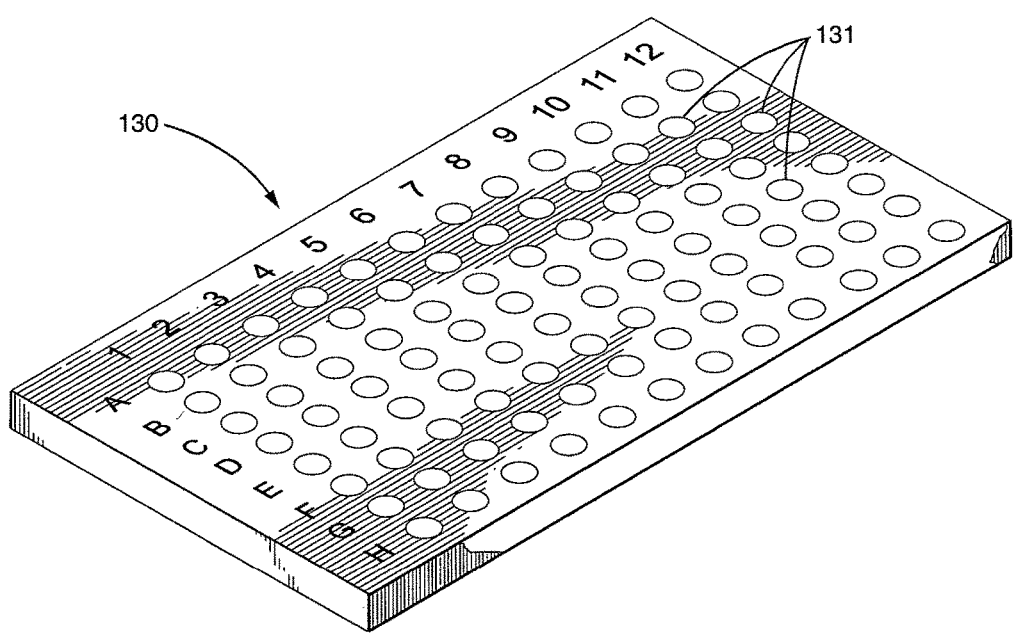
FIG. 4 illustrates a 96-well sample plate that is used to hold liquid samples for interrogation by a cytometer.

Flow and scanning cytometers are being used with increasing frequency in applications that require a large number of samples to be interrogated. Consequently, the Guava EasyCyte Plus and other cytometers are designed to automatically interrogate a multiplicity of samples in a multi-well sample plate or alternative multi-sample carrier. FIG. 4 is a schematic representation of a 96-well plate 130 with sample wells 131 in a regular array of rows and columns. Plates similar to the plate 130 are commonly used for the automated interrogation of multiple liquid samples. With six detectors, a single run with a full 96-well plate generates 96 six-parameter data files.

Figure 5:
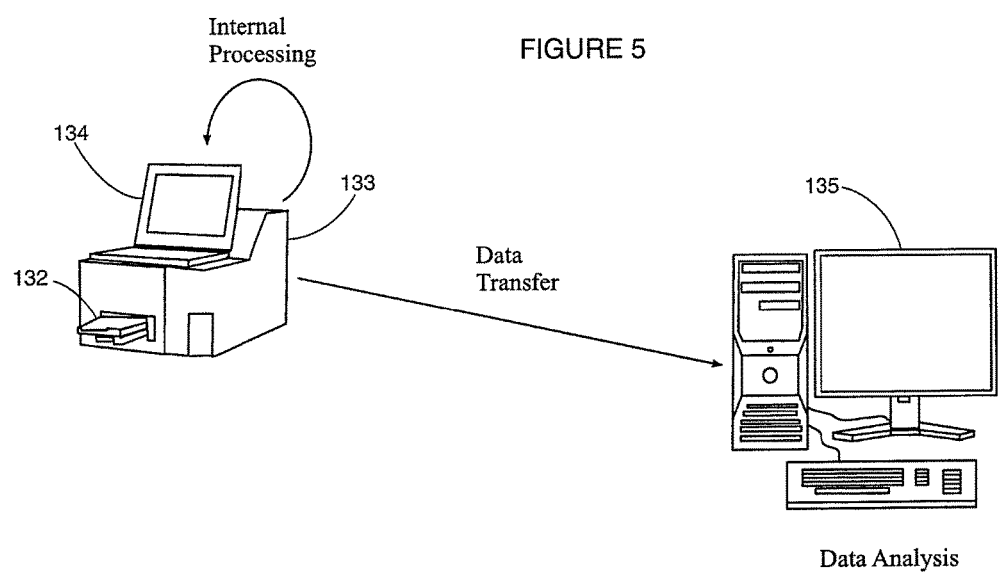
FIG. 5 illustrates a system for the interrogation of multiple samples using a flow cytometer and the analysis, display and comparison of the interrogation data.

FIG. 5 is a schematic representation of a hardware and data transfer scheme that may be utilized for the automatic interrogation of a multiwell sample plate with a flow cytometer and the analysis of the interrogation data. In a typical measurement, a multiwell sample plate similar to the plate 130 of FIG. 4 is loaded into the plate carrier 132 of a flow cytometer 133 by an operator (not shown). Measurement parameters, storage format, sample specifications, and other data are entered into the digital control unit 134 of the cytometer by the operator. In some instruments, the digital control unit 134 is incorporated into the cytometer package or alternatively, the digital control unit 134 may be a computer.

Interrogation data and other information is typically stored in a predefined file format and may be transferred to computer 135 for analysis and comparison. Alternatively, it may be analyzed by the digital control unit 134. In cases where a computer 135 is used for data analysis and comparison, data is transferred from the flow cytometer 133 to the computer 135 using conventional methods that include but are not limited to optical discs, magnetic drives, flash drives, Ethernet connections, USB connections, Fire wire connections, wireless networks and Internet connections.

Conventional cytometry analysis packages allow the user to select a group of data files for analysis from a list or, in some cases, from a visual representation of the sample carrier. These packages also allow a group of data files to be analyzed using one or more common gate definitions but do not allow a user to visually compare the output data. Instead, the output data is tabulated in a spreadsheet and/or transferred to a generic visual presentation application.

Cytometer users who interrogate a large number of samples often add biological compounds to wells on a sample plate in such a way that wells containing a specific compound form a geometric shape on the sample plate. The central representation 140 in FIG. 6, for example, is a map of a square arrangement of 64 wells in sample plate that have been filled with identical samples of $CD8^+$ cells. The hatched regions 142 in the outer plate representations 144 correspond to sub-arrangements of wells in which the indicated cytokine has been added to each well. The central plate representation 140 illustrates the combination of cytokines in each well. Once cytokines are added to the samples in a multi-well plate according to the map 140 in FIG. 6, they may be interrogated in a single automated run by a cytometer such as the Guava EasyCyte Plus flow cytometer and the results stored in 64 input data files. If the six detectors of the EasyCyte Plus instrument are used to record data during the interrogation, each event in an input data set may be represented as a six-dimensional vector. Analysis of these files for CCR7 expression, for example, is accomplished by defining a volume in the six-dimensional data space with one and two dimensional gates and counting the number of events in each data file that lie within the gated volume.

Figure 6:
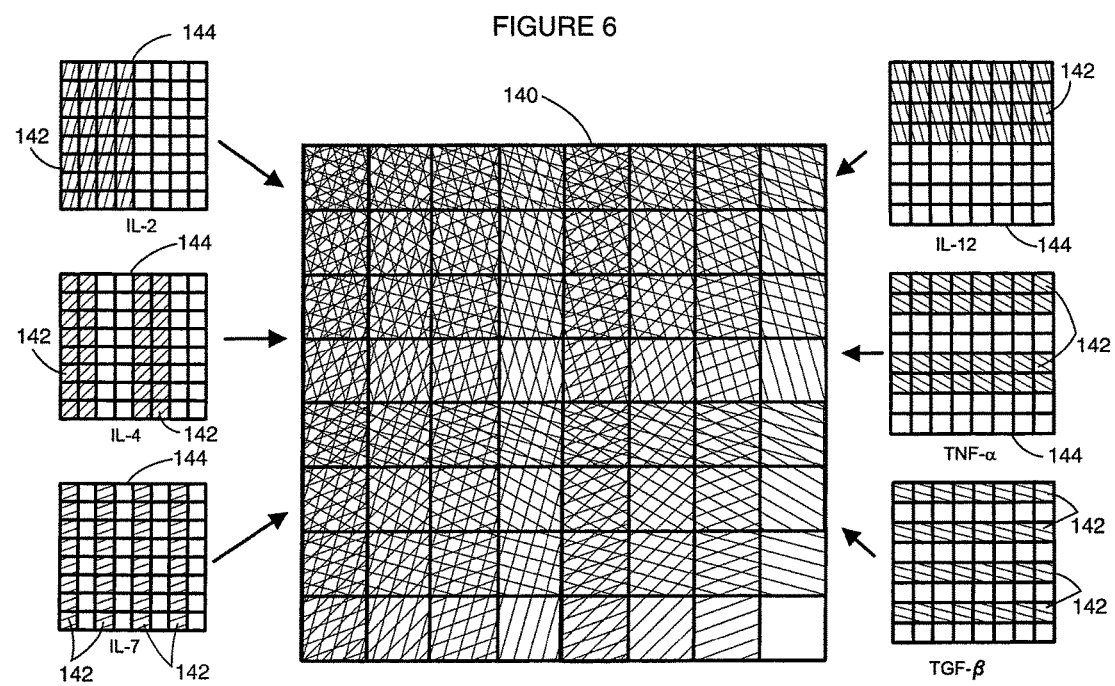
FIG. 6 illustrates a pattern of adding of six cytokines to identical samples in 64 sample wells to determine the effect of the cytokines the cellular processes in the samples.

Conventional cytometry analysis packages present the analysis results in a tabular format that makes it difficult for an operator or data analyst to correlate the output information with the position of the sample in the multi-well plate. In the experiment of FIG. 6, for example, information associated with the well location is very difficult to extract from a tabular presentation of output data.

Conventional cytometry analysis packages also force the operator or data analyst to numerically compare the output data from different samples or analyses. In cases where it is desirable to compare data from several plates of samples or to simultaneously evaluate the results obtained by applying a plurality of analyses to a single group of samples, the numerical comparison of output data is both difficult and time consuming.

The analysis and display of data that is obtained by interrogating a number of sample locations is significantly complicated without the ability to compare two or more sets of location-specific data. In cytometry and other applications, sample locations often have a fixed spatial relationship to one another and the individual carrying out the interrogation and/or analysis can quickly identify the properties of a sample by its relative location to other samples. The experiment illustrated in FIG. 6 is representative of many experiments in which cytokines or other substances are added to samples on a carrier according to their location and automatically interrogated using a flow cytometer.

Figure 7:
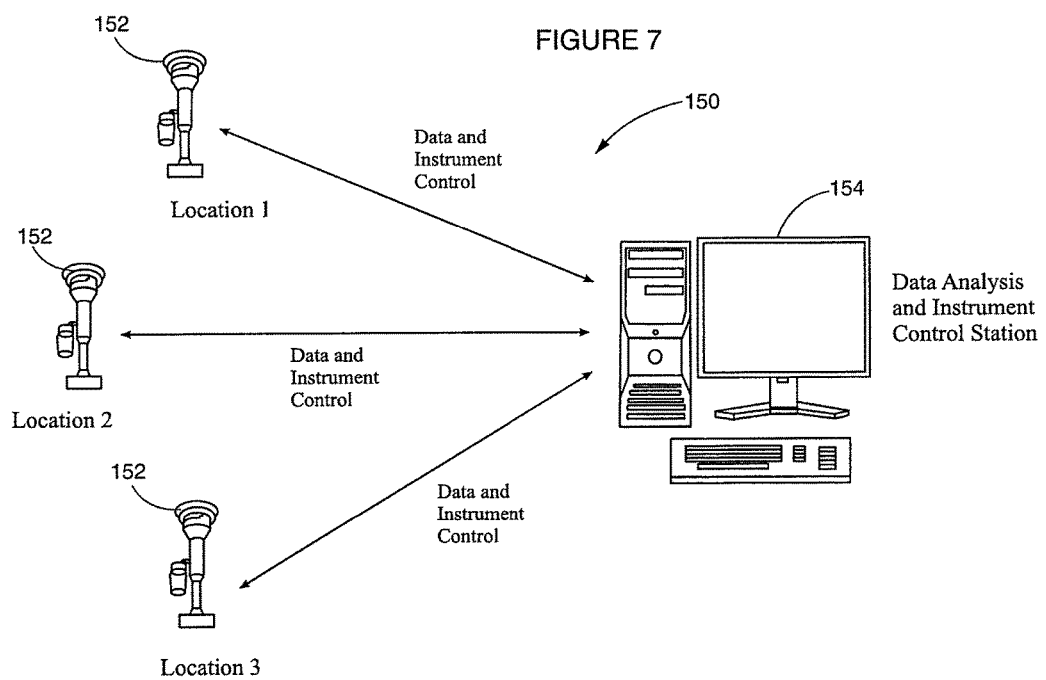
FIG. 7 illustrates a system for the interrogation of the atmosphere at three locations using pollution monitors and the analysis, display and comparison of the interrogation data.

In other applications of the sort of data analysis described above, two or more instruments may be used to interrogate samples. For example, the concentration of air pollutants including PM2.5, PM10, ozone and sulfur dioxide may be measured by a spatial arrangement of pollution monitors at locations within a city or other geographic area. The location of the instruments may be easily displayed by superimposing an arrangement of icons similar to the arrangement of instrument locations on a map. FIG. 7 is a schematic illustration of the hardware and communication channels in a representative pollution monitoring system 150. In the illustrated system, instruments 152 that monitor the concentrations of two or more pollutants are positioned at different locations. The instruments 152 are controlled by a central computer 154 that is also used for data analysis and comparison of the analyzed data. Information may be transferred between the central computer 154 and the monitoring instruments 152 using conventional methods.

These computer interfaces do not allow a user to visually correlate output data with sample locations and compare multiple sets of output data from one or more sample locations. In conventional interfaces, output data sets are commonly presented in a tabular form with specific locations designated by numerical and/or alphanumeric characters. Tabulated data may be subsequently displayed using a commercial graphical presentation package but such packages do not have the ability to simultaneously display multiple data sets in terms of the position of the samples from which the data was derived. These user interfaces wherein data is visually presented according to sample location only allow a single data set to be displayed and precludes the visual comparison of two or more data sets.

Figure 8:
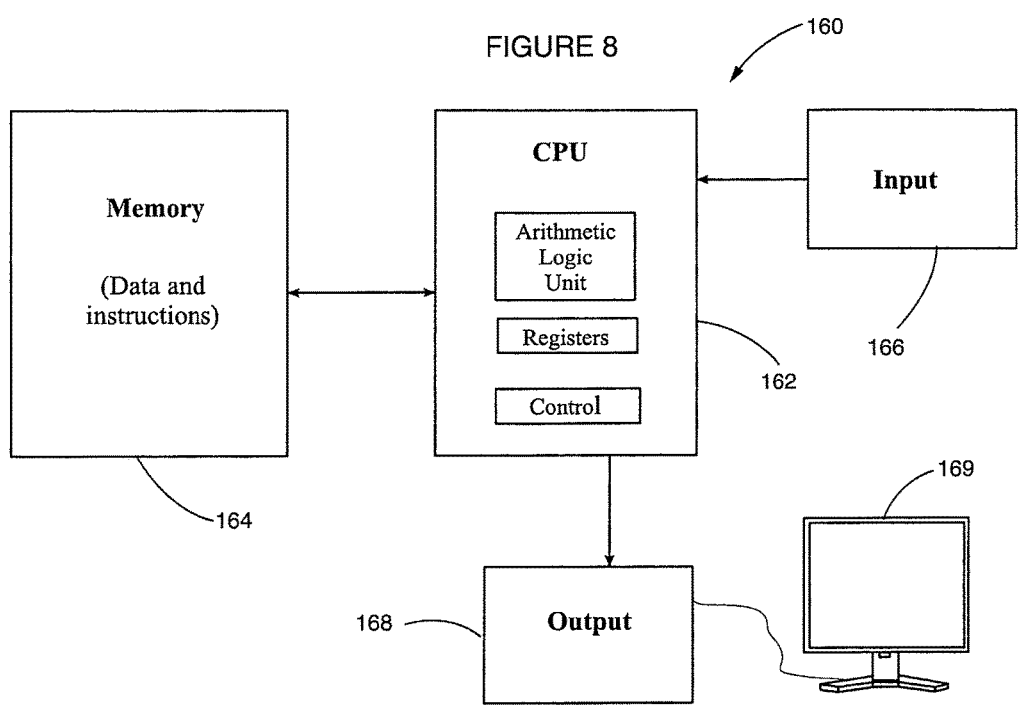
FIG. 8 illustrates the architecture of a digital computer.

According to the invention, a user controls the analysis and display of data to enable the visual comparison of multiple data sets in terms of the positions of the samples from which the data were gathered. The visual comparison is provided by a digital computer having the basic architecture illustrated in FIG. 8 or an alternative architecture capable of performing the functions of the FIG. 8 architecture. In the illustrated architecture 160, a user typically controls the central processing unit (CPU) 162 and memory 164 by interacting with devices that are represented by the input block 166 and output block 168. For example, input operations may be accomplished using a conventional keyboard and pointing device, trackball, touchscreen display, digitizing tablet or alternative human interface devices. Output from the CPU 162 is directed to the output block 168, which connects to a display 169 and may also connect to one or more networking devices such as an Ethernet, Internet or wireless network connection and storage devices such as a magnetic disc, flash memory, or optical disc. Digital computers suitable for the practice of the invention include, for example, desktop or laptop personal computers of the type commonly employed for routine instrument control and data analysis or multiuser machines such as mainframe computers. Suitable displays include, but are not limited to, LCD and TFT flat panel displays, plasma displays, CRT displays, projection displays, and interfaces that allow computer generated images to be viewed on conventional television sets.

Figure 9:
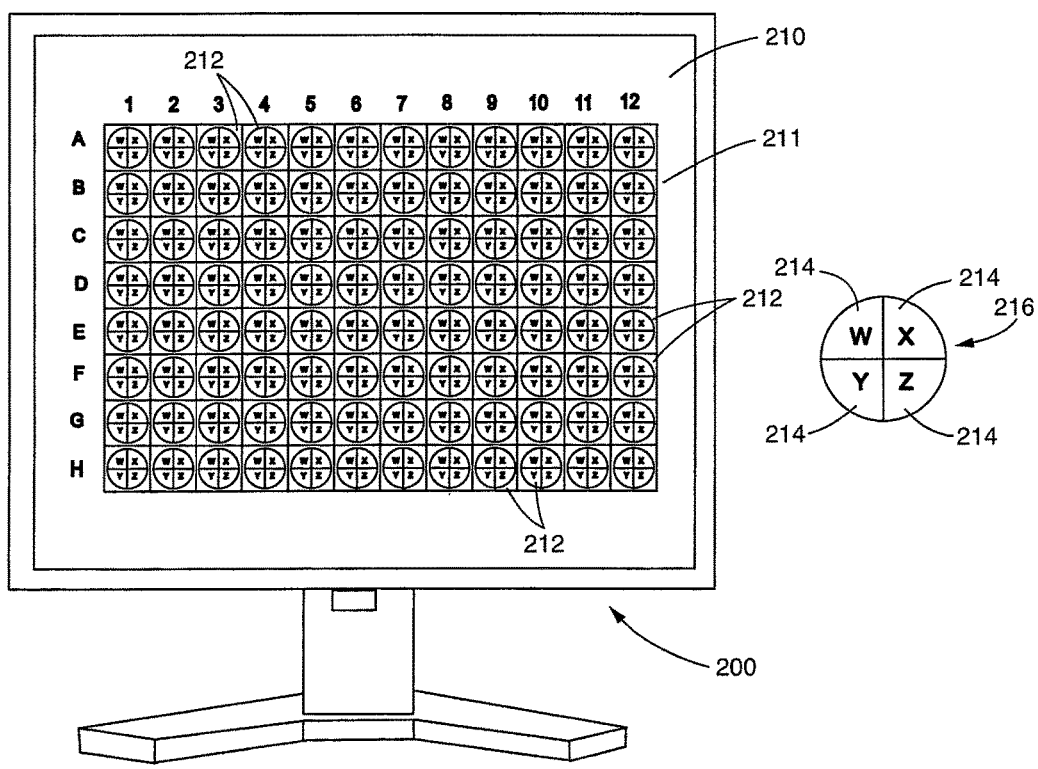
FIG. 9 illustrates an arrangement of icons on the screen of a computer display that is similar to the arrangement of wells in a 96-well sample plate and the division of the icons into regions that may be used to visually represent output data sets.

In one embodiment, the present invention provides a user interface for the simultaneous display and visual comparison of multiple sets of location-specific data. According to the invention, the results from two or more analyses of location specific interrogation data may be displayed on a computer output device using a novel, location-specific, multiplexed heat map, as illustrated in FIG. 9. In the screen 210 of the computer display 200 illustrated in FIG. 9, a multiplexed heat map 211 is used to visually present data obtained by interrogating particle-containing biological samples in the wells 131 of the 96-well sample plate 130 of FIG. 4 with a flow cytometer. In the multiplexed heat map 211, the wells 131 are represented by an arrangement of circular icons 212 that is similar to the arrangement of wells 131 in the 96-well sample plate 130. The similarity of the arrangements of the icons and the wells allows a user interacting with the computer interface to visually associate each of the icons 212 in the interface 210 with a sample well.

In the location-specific multiplexed heat map 211, each of the icons 212 is divided into four regions 214 as illustrated in the icon detail 216. The regions 214 in the icon detail 216 and the map 211 are labeled W, X, Y, and Z. Output data sets containing results from the analysis of input data from at least one sample are visually presented in each region. In a case where each of the wells 131 of the sample plate 130 contains a sample that is interrogated using a flow cytometer, the multiplexed heat map may be used to visually present the results of four different analyses of the interrogation data.

In an alternative case where each of the wells 131 of two different sample plates, similar to the 96-well plate 130, are interrogated and analyzed using two different analyses, regions W and X of the icons 212 may be used to represent the results obtained by analyzing data from one sample plate and regions Y and Z of the icons 212 may be used to represent the results obtained by analyzing data from the other sample plate. In a further example, where each of the wells 131 of four different sample plates, similar to the sample plate 130, are interrogated and analyzed using a single analysis, a data set associated with the wells on each one of the plates may be visually presented in a unique region of the icons 212.

In keeping with the invention, data presented in an icon are derived from analyses of the input data obtained by interrogating a sample location associated with the icon. Information associated with the position of a sample is, therefore, inherent in the visual presentation of the output data in a location-specific, multiplexed heat map. This may be contrasted to a multiplexed heat maps in which the position of an element or icon within the heat map is associated with an experimental variable or the value of an experimental variable.

Within each region, the results of an analysis may be represented using known techniques. For example, a range of numerical magnitudes may be visually presented as variations in visual tone or color. When values are presented in this fashion on a computer display, a user with normal vision may visually determine values with an accuracy of approximately 10%. We have discovered that a large dynamic range of values may be visually represented with increased precision if the logarithms of the values are represented by variations in visual tone or color. We have further discovered that the accuracy of both linear and logarithmic representations may be advantageously increased by superimposing hatched patterns on the visual tone or color representation.

Figure 10:
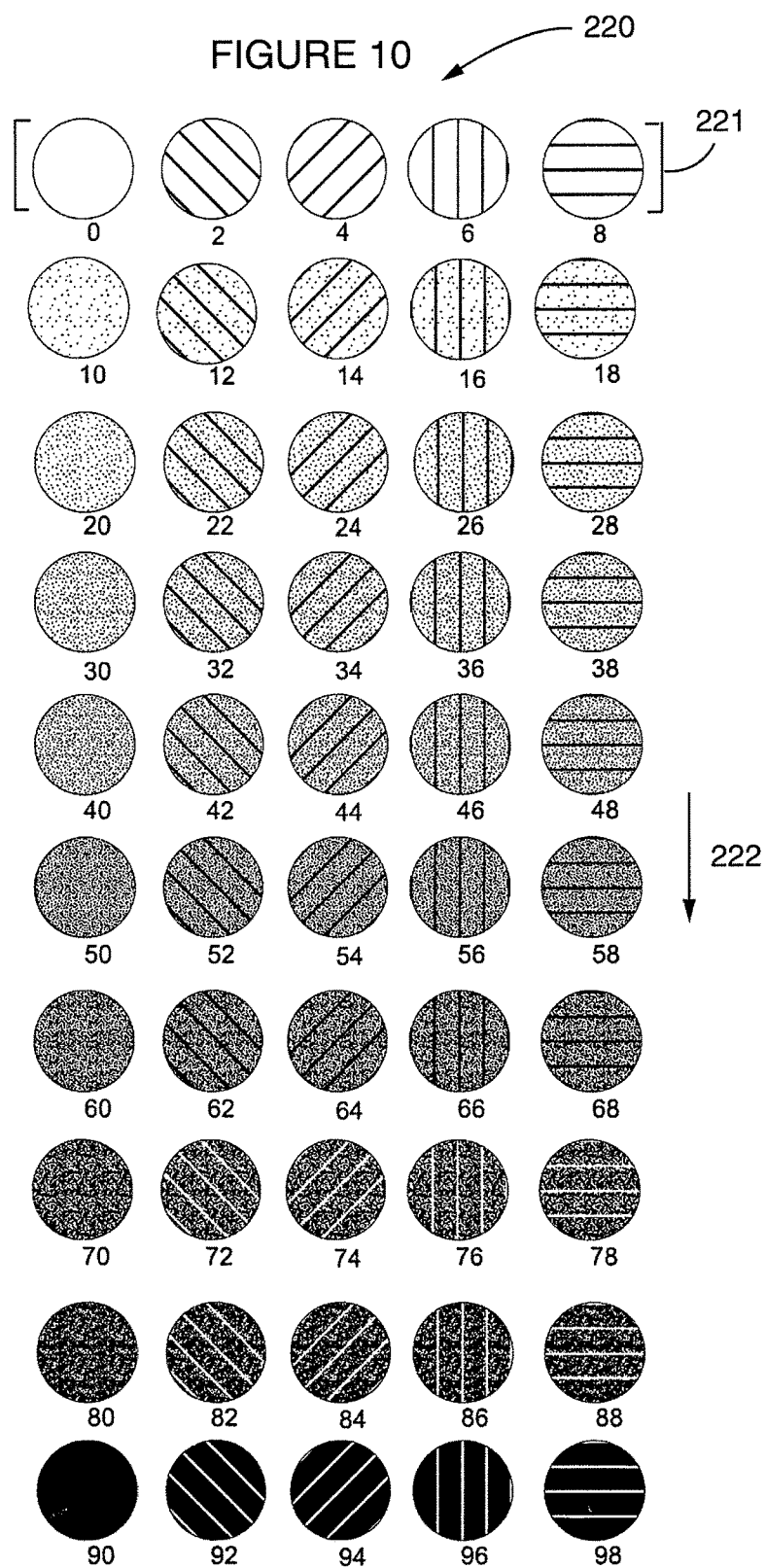
FIG. 10 illustrates the visual representation of numerical values with a combination of visual tone and hatched patterns.

FIG. 10 illustrates the representation of numerical values using a combination of optical density and hatched patterns. In the topmost row of the hatched optical density scale 220, the zero representation is unhatched and the values from two units to eight units are represented in increments of two units by different hatched patterns. Moving down the scale 220 from the topmost row 221 in the direction 222, the increase in optical density in adjacent rows represents an increment of ten units. In this manner the scale 220 visually represents values from zero to 98 units with ten levels of optical density and four hatched patterns. In the illustration of FIG. 10, stippling of varying density is applied to each of the columns of icons in order to show varying gray scale or color. The stippling is employed in FIG. 10 to accommodate limitations imposed by the requirements for drawings in US patent applications. In typical embodiments of the invention, however, the variations in the optical density illustrated by the varying density of stippling in the scale 220 of FIG. 10 are replaced with variations in continuous visual tone or color to facilitate visual discrimination of different values on a conventional computer display. Further increases in resolution are possible using scales with a larger number of hatched patterns.

Figure 12:
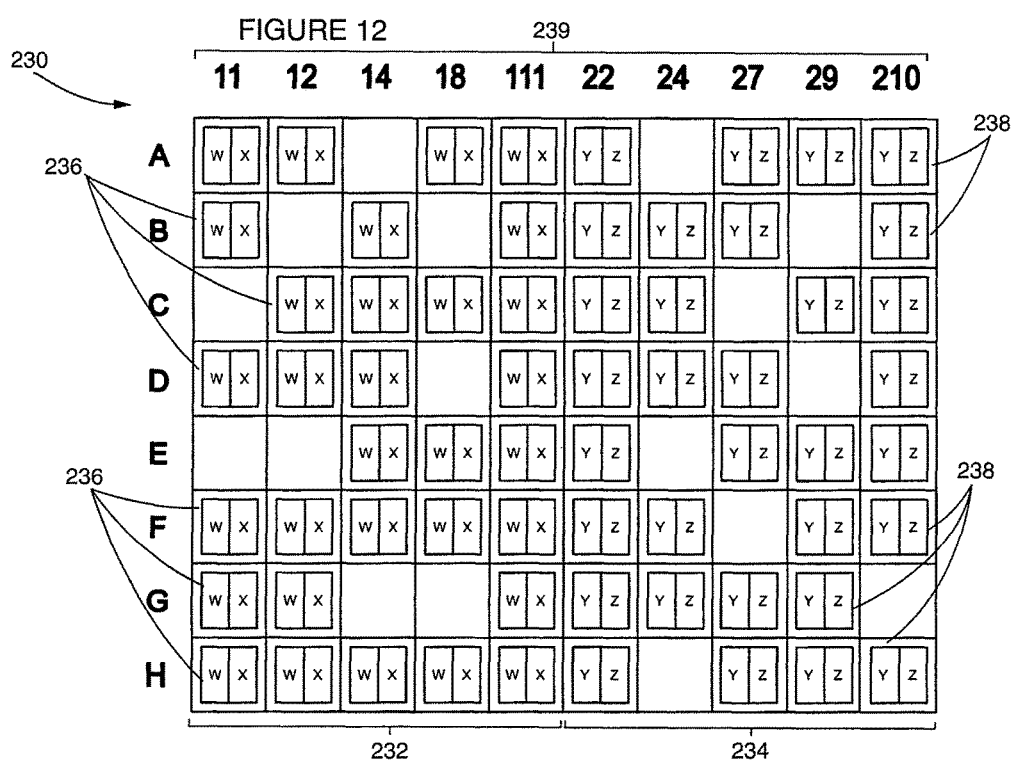
FIG. 12 illustrates an arrangement of square icons associated with the locations on the sample plates of FIG. 11 and the division of the icons into regions that may be used to visually represent data sets resulting from analyses of data obtained by interrogating the associated locations on the sample plates.

In alternative embodiments of a location-specific, multiplexed heat map in keeping with the invention, output data associated with two or more arrangements of sample locations may be presented. FIG. 11 illustrates two different arrangements of sample locations 224, 226 on two 96-well plates. FIG. 12 illustrates one of several alternative multiplexed location-specific heat maps that may be used to display output data resulting from the interrogation and analysis of input data from the wells in FIG. 11. In the map 230, square icons 236 in a first group of five columns 232 represent the sample wells on the sample plate 224. Square icons 238 in a second group of five columns 234 represent the sample wells on the sample plate 226. In the map 230, representations of empty columns have been omitted and numerical labels 239 used to designate the sample plates and columns on the sample plates that are represented by the columns on the map 230.

Results from two analyses of the data obtained by interrogating the sample locations on the sample plate 224 are visually presented in the regions of the icons 236 in the first group of five columns 232 in the map 230. Results from one analysis are presented in the region of the icons labeled 'W' and results from the other analysis are presented in the region of the icons labeled 'X.'

Similarly, results from two analyses of the data obtained by interrogating the sample locations on the sample plate 226 are visually represented in the regions of the icons 238 in the second group of columns 234. Results from one analysis are presented in the region of the icons labeled 'Y' and results from the other analysis are presented in the region of the icons labeled 'Z.' The same analysis may optionally be used to generate the output data represented in regions 'W' and 'Y' and, similarly, a second analysis may optionally be used to generate the output data in regions 'X' and 'Z.'

Within each region of the map 230, the results of an analysis are visually represented using known techniques. Typically, numerical magnitudes are visually represented as variations in visual tone or color. In cases where the represented values cover a large range, it is possible to increase the accuracy of the representation by representing the logarithms of the values. The resolution of both logarithmic and linear representations can be increased by superimposing hatched patterns over tonal or color representations.

Figure 13:
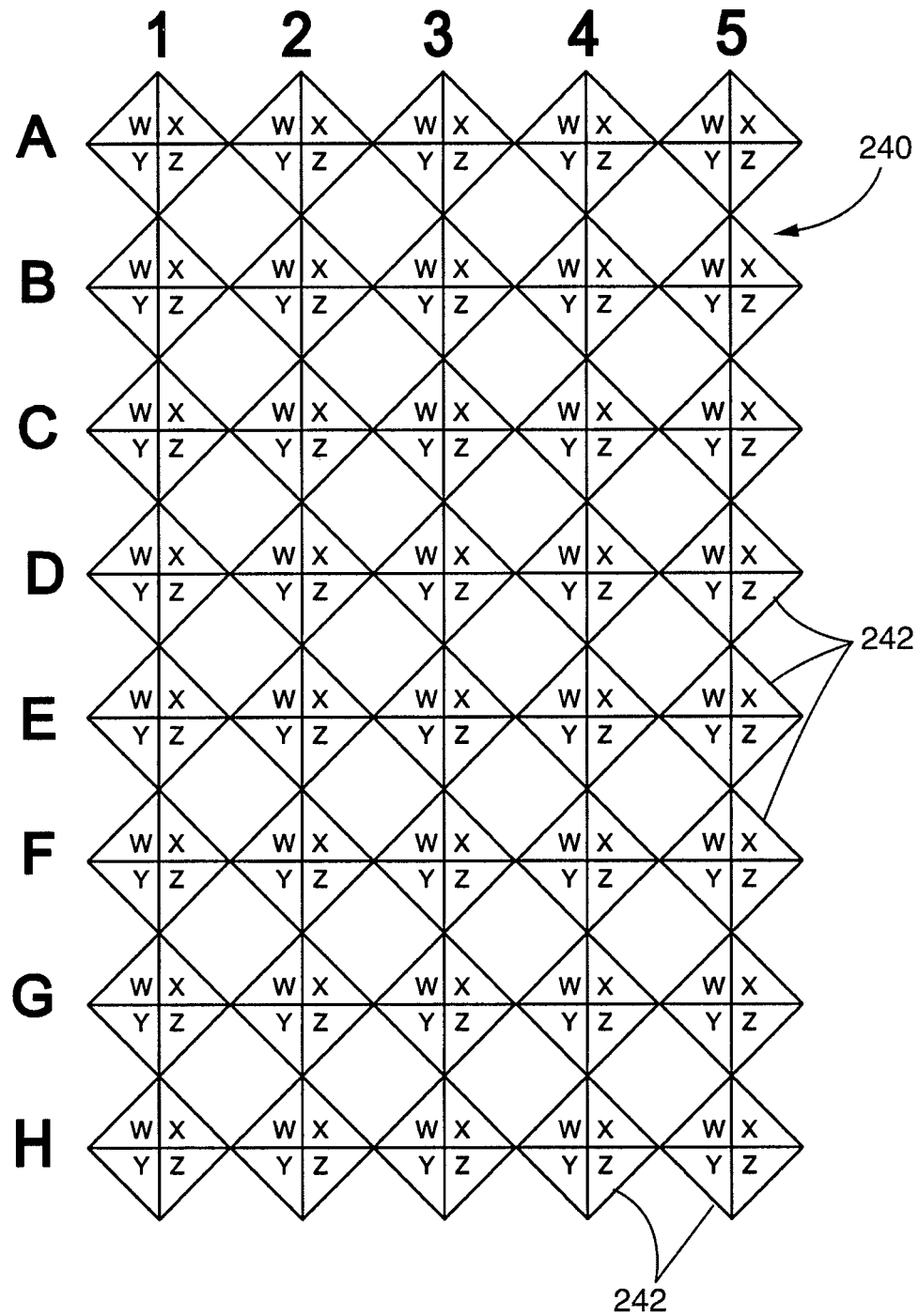
FIG. 13 illustrates an arrangement of diamond-shaped icons associated with the locations on the sample plates of FIG. 11 and the division of the icons into regions that may be used to visually represent data sets resulting from analyses of data obtained by interrogating the associated locations on the sample plates.

FIG. 13 illustrates another embodiment of the invention in which results obtained by interrogating and analyzing data from the sample locations on the plates 224 and 226 are presented in a 5 column, location-specific, multiplexed heat map 240. In this embodiment, sample locations are associated with diamond-shaped icons 242 that are divided into four regions. Data from the interrogation and analysis of the sample locations on sample plate 224 are visually represented in the regions labeled 'W' and 'X' and data from the sample locations on sample plate 226 are visually represented in the regions labeled 'Y' and 'Z.' Within each region, the results of an analysis may be visually represented using various techniques as previously described.

While FIGS. 9, 12 and 13 illustrate the key features of the location-specific, multiplexed heat map invention, the invention may be practiced using a wide range of sample locations and icon arrangements, icon shapes, and schemes for dividing the icons into regions. The illustrated arrangements of samples in a 96-well sample plate represent a small subset of the sample arrangements that may be represented in a location-specific multiplexed heat map.

In general, sample arrangements may be asymmetrical and lack any recognizable pattern or they may be symmetrically arranged in circular, square, rectangular, triangular or other more complex patterns. Icons may have any closed shape including ellipses, regular and irregular polygons having three or more sides, or icons may have shapes resembling the outline of objects, animals, humans, scientific instruments or geographic features. Icons may be divided into any number of regions and the areas of the regions within an icon may be approximately equal but need not be. Icons may be divided into any number of regions by straight or irregular lines, arcs or other divisions. Experimentally, maps with icons of eight or fewer divisions have been found to offer advantages with respect to numerical resolution over maps having a greater number of regions. Icons may be arranged in any fashion that allows the user of the interface to visually associate the icons with the sample locations.

The quantitative visual representation of results in a location-specific, multiplexed heat map requires the assignment of each set of analysis results to a region in the map. It further requires units of measurement to be assigned to each set and a range of values be specified for the visual representation in each region. The interface may automatically assign units of measurement and specify a range of numerical values for each of the regions or a user may carry out these tasks by interacting with one or more control panels in the interface. Control panels may allow ranges and units to be entered using a keyboard or it may allow a user to use a pointing device to move sliders, knobs, or other control representations in the interface.

Figure 14:
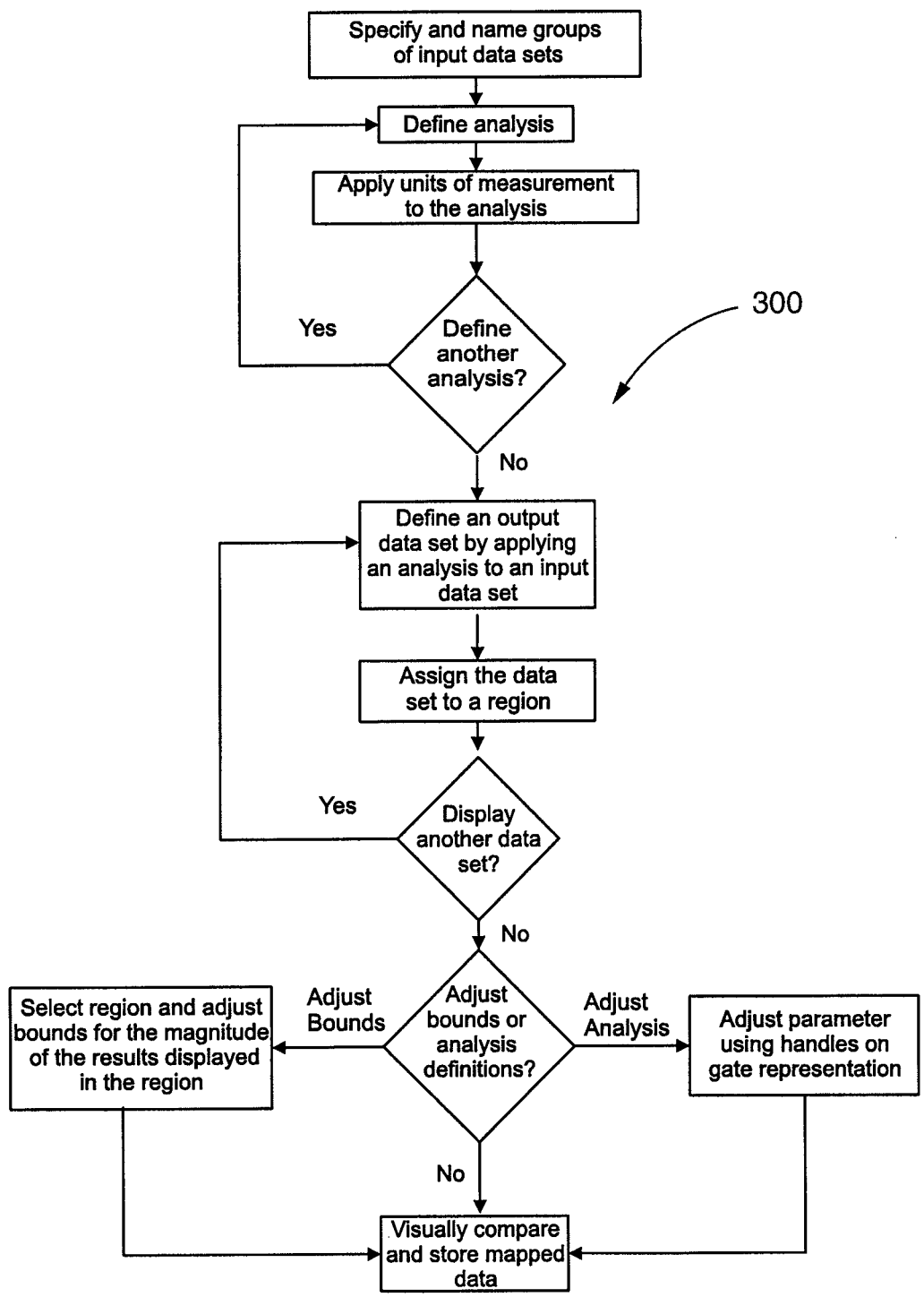
FIG. 14 is a flow chart representing the process of selecting, analyzing, and visually representing results obtained by analyzing location-specific flow cytometry data.

FIG. 14 is a flow chart detailing the principal steps in a process 300 for using the invention to define analyses and visually compare the results obtained by applying the analyses to data resulting from the interrogation of biological samples in at least one multiwell plate using a cytometer. In one embodiment of the invention, this process is carried by a user who interacts with a computer interface comprising a number of interactive displays or 'screens.' The user typically interacts with the interface using a conventional computer keyboard and pointing device such as a mouse or trackball. The mouse or trackball allows the user to carry out standard interface operations including 'point and click' and 'click and drag' operations. In some embodiments of the invention, however, users may interact with the interface through alternative human interface devices including touch screen displays, digitizing tablets, touch pads and motion sensors.

Figure 15:
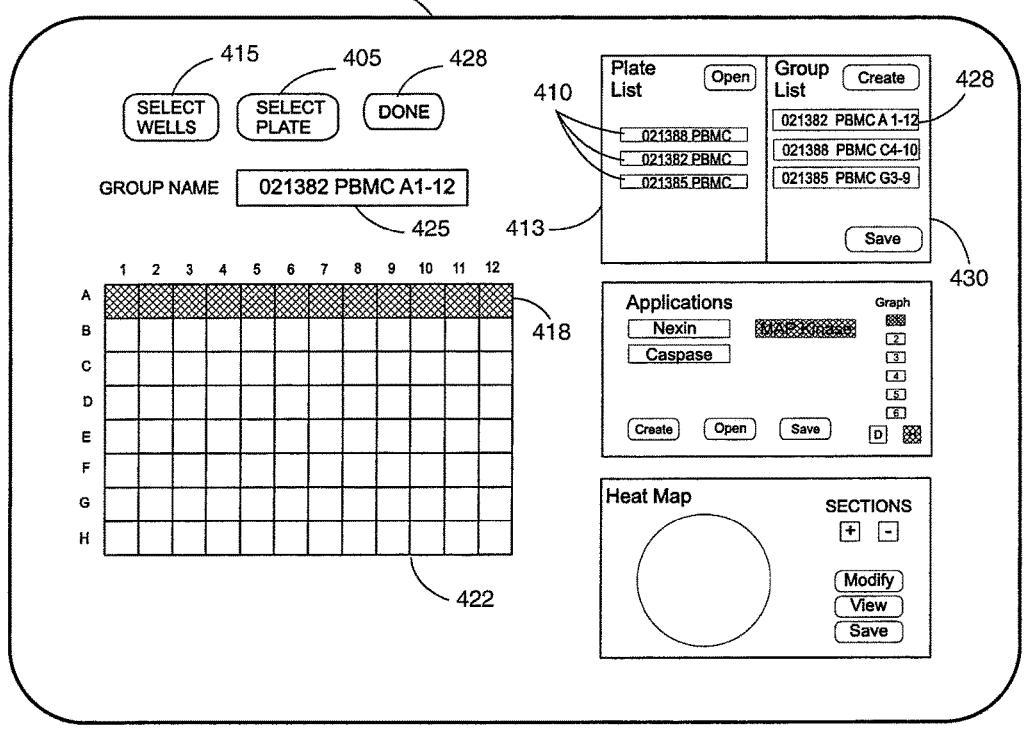
FIG. 15 illustrates a group selection screen in a user interface.

In the process 300, the user initially defines groups of input data sets for analysis by specifying sample locations or other input data set identifiers. This may be accomplished, for example, through interaction with a group definition screen 400 as illustrated in FIG. 15. In the screen 400, groups are specified by activating the 'SELECT PLATE' button 405 and selecting one of the plate designators 410 in the Plate List box 413. Activation of buttons and selection of designators within the interface is typically accomplished by positioning a cursor over the designator and 'clicking' on the button or designator with a mouse or by executing a similar operation with an alternative human interface device.

After selecting a plate, the user activates the 'SELECT WELLS' button 415 and specifies the wells from the displayed plate that will be included in the group. In the interface screen 400, wells are specified by selecting a group of well representations, such as the shaded group of well representations 418, in the schematic plate representation 422. The wells are typically selected using a standard 'point and click' operation with the mouse or alternative human interface device. Wells from additional plates may be added to the group by activating the 'SELECT PLATE' button 405, selecting a different one of the plate designators, 410, activating the 'SELECT WELLS' button 415 and selecting a group of well representations from the plate representation 422. When all wells in the group are selected, a group name is typically entered into the 'GROUP NAME' box 425 and the group closed by activating the 'DONE' button 428. Activation of the 'DONE' button also generates a group designator 428 containing the group name in Group List box 430.

Figure 16:
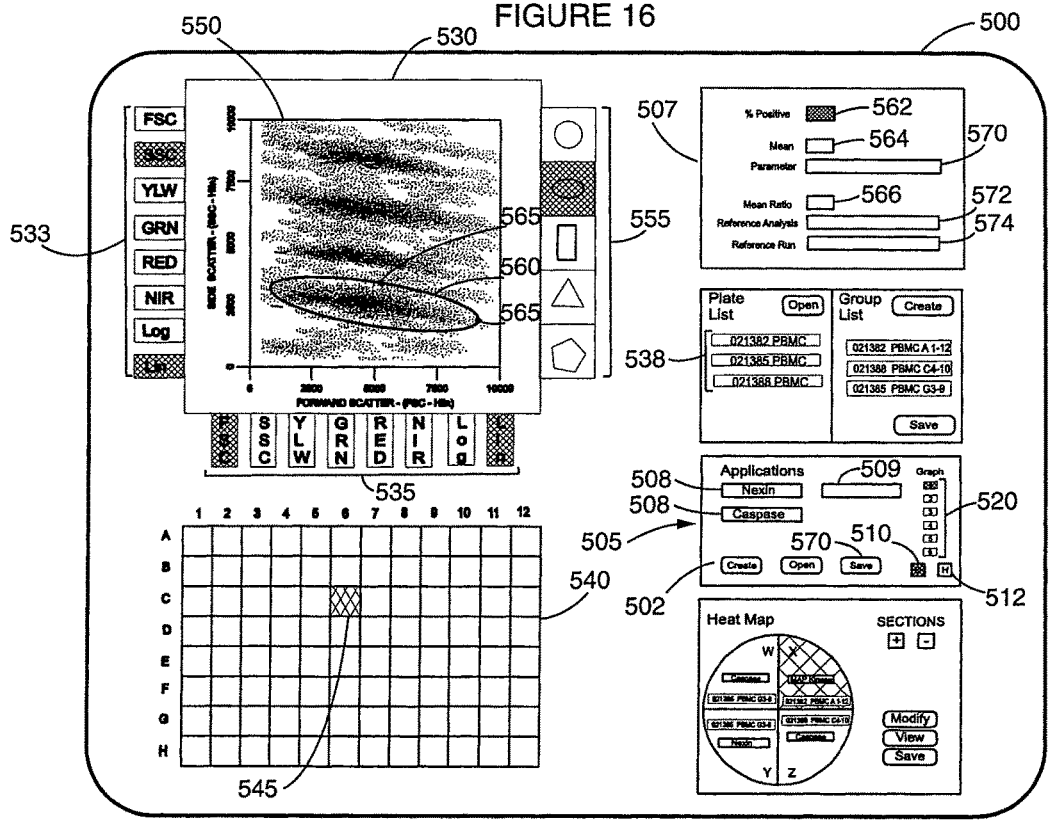
FIG. 16 illustrates an analysis definition screen in a user interface.

In the process 300, the step of specifying and naming groups is followed by the step of defining an analysis and applying units of measurement to the analysis. This may be accomplished by interacting with an analysis definition screen 500 as illustrated in FIG. 16. When the analysis has been previously defined, a user may recall the analysis and select it using one of the application designators 508 in the Applications box 505. Alternatively, a user can define a new analysis by activating buttons and entering parameters in the Applications box 505, entering parameters in the unit assignment box 507, and interacting with the gate definition graph 530 and the heat map 540.

To create a new analysis, a user activates the 'Create' button 502 in the Applications box 505. Activation of the Create button 502 adds a blank analysis designator 509 to the analysis designators 508. Histograms or dot plots similar to histogram 110 of FIG. 2 and the dot plot 120 of FIG. 3 are then used to define each gate in the analysis. In screen 500, a user may specify 6 or fewer individual gate definitions The gates are automatically combined using the logical operator AND in such a way that an analysis, A, satisfies the following logical equation:

A=(Gate 1) AND (Gate 2) AND (Gate 3) AND (Gate 4) AND (Gate 5) AND (Gate 6).

Analyses with fewer than 6 gates are similarly defined by combining the defined gates with the logical operator AND.

In alternative embodiments, the screen 500 includes a function definition box (not shown) that allows a user to enter a logical gate definition equation. Exemplary function definition boxes have a list of gates that are separated by pull-down menus or by direct input fields allowing a user to specify a gate definition equation by selecting logical operators from the pull-down menus or entering them in the input fields. Alternatively, the function definition box contains a field where the user can directly enter the gate definition equation.

To define a gate in an analysis, a user initially specifies the gate number by activating one of the graph selection buttons 520 and selects a graph type by activating the dot plot, 'D' button 510 or the histogram, 'H' button 512. In FIG. 16, the dot plot button 510 has been activated.

Activation of one of the graph selection buttons 520 in combination with the dot plot button 510 or the histogram button 512 results in a graph of the appropriate type being displayed in the gate definition window 530. Axes for the graph in the gate definition window are selected by activating one or more of the vertical axis designation boxes 533 and one or more of the horizontal axis designation boxes 535. Data for the gate definition process is selected by activating one of the plate designators 538 and subsequently selecting a sample location in the plate map 540. In the screen 500, the selected sample location 545 has been hatched. Upon selection, input data from the designated sample location 545 is plotted in a graph 550 with the selected axes in the gate definition window 530. A gate is defined by activating one of the gate shapes 555 and adjusting the location, size and orientation of the FIG. 560 by clicking and dragging the handles 565.

Gate buttons 520 are activated and the gate definition process repeated until all gates in the analysis have been defined. Units are then assigned to the analysis by activating the '% Positive' button 562, the 'mean' button 564, or the 'Mean ratio' button 566 in the unit assignment box 507. If the '% Positive' button 562 is activated as it is in the screen 500, no additional information is required to assign units to the region. In cases where the 'Mean' button 564 is activated, an axis or parameter must be specified in the Parameter box 570. In cases where the 'Mean ratio' button 566 has been activated, an axis or parameter must be specified in the Parameter box 570, a reference analysis must be specified in the Reference Analysis box 572 and a reference sample position and plate must be specified in the Reference Run box 574. The analysis definition process is terminated by entering an analysis name in the analysis designator box 509 and activating the 'Save' button 570 in the Applications box 505.

Figure 17:
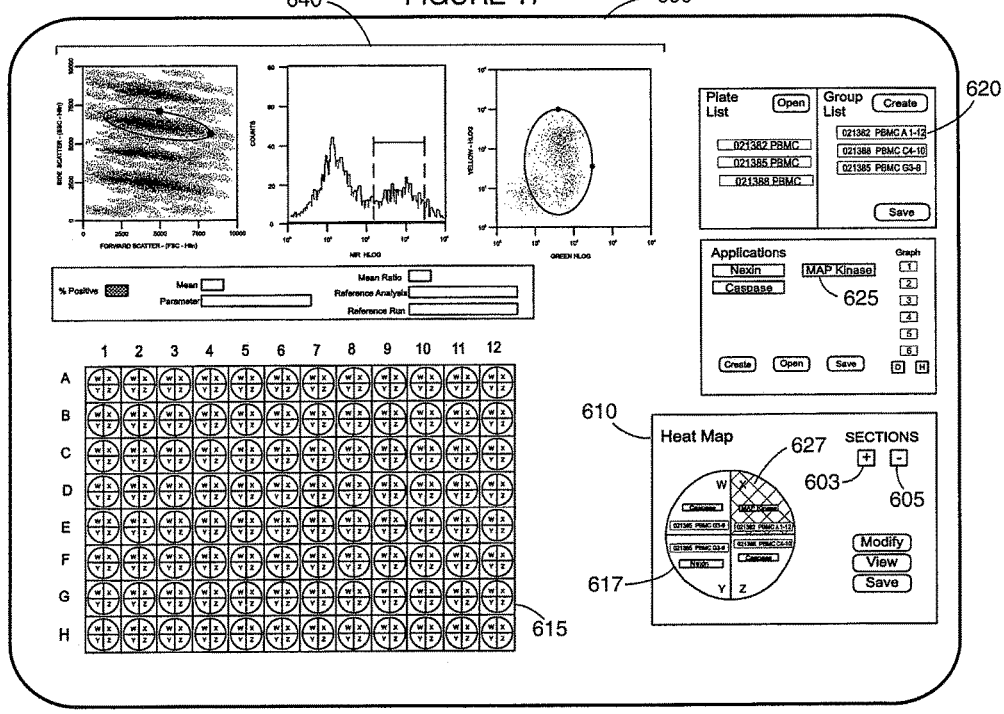
FIG. 17 illustrates a heat map definition screen in a user interface.

In the process 300, output data sets are generated by applying an analysis to a group of input data sets. To display and visually compare two or more output data sets using a location specific, multiplexed heat map, the data sets must be assigned to regions in the map and units of measurement and bounds on the range of displayed values specified for each set. A user may generate output data sets and assign them to regions in a location-specific, multiplexed heat map by interacting with a screen 600 in the user interface as illustrated in FIG. 17. Using this screen, the user specifies the number of output data sets to be included in the visual presentation by activating the '+' button 603 or '−' button 605 in the Heat Map box 610. Regions are added to the icons of the heat map 615 and the icon representation 617 by activating the '+' button and removed by activating the '−' button. In a typical case, the icons initially have a single region (undivided icons) and the user repetitively activates the '+' to obtain a desired number of regions. The icon representation 617 in the Heat Map box 610 is divided in the same fashion as the icons in the heat map 615. Output data sets are specified by dragging a group designator 620 and an analysis designator 625 into one of the regions of the icon representation 617. In the screen 600, for example, the group designator 021382 PBMC A1-12 620 and the analysis designator MAP Kinase 625 have been dragged into region X 627 of the icon representation 617 to define the output data set that is generated by applying the MAP Kinase analysis to the group 021382 PBMC A1-12.

Dragging a group designator and an analysis designator into the a region of the heat map representation 617 activates the region as illustrated by hatching in the region X 627 of the icon representation 617 in the screen 600, visually represents the output data set values in region X of the heat map 615, and displays the graphs 640 defining the analysis. The maximum numerical value in the data set is automatically determined by the user interface and the range of values between zero and the maximum value in the data set are visually represented in the region X of the heat map 615. Additional output data sets may be assigned to regions of the heat map 615 by dragging and dropping other group/application combinations into the regions W, Y and Z of the icon representation 617.

After assigning and visually representing two or more output data sets in the regions of the location-specific, multiplexed heat map 615, comparison of the data sets may be facilitated by expanding the heat map 615 in such a way that it fills the screen of the computer display. When displayed in this fashion the inventive heat map allows the user to compare global features of the data sets and relate these features to the sample positions from which the output data was derived.

Figure 18:
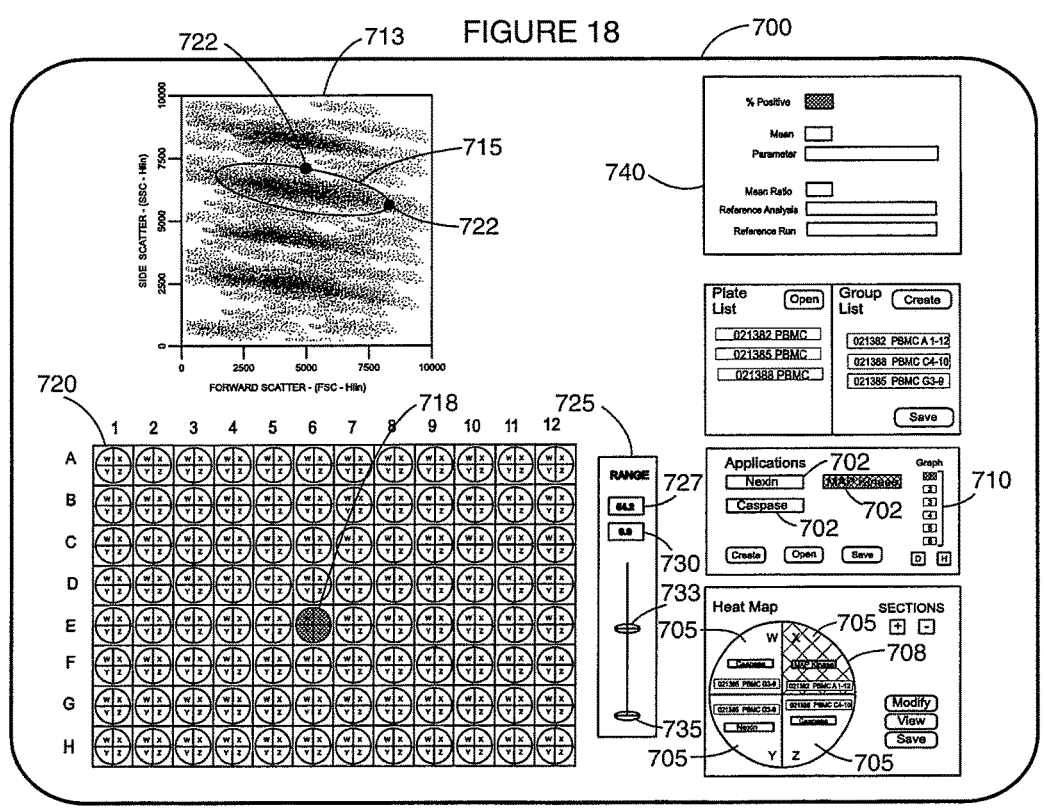
FIG. 18 represents a gate modification screen in a user interface.

In certain cases, a data comparison may indicate that the gate definitions or the range of represented output values require optimization. A user may accomplish this task by interacting with a screen similar to the screen 700 of FIG. 18. In the screen 700, an application is specified by activating either an analysis designator 702 or a region 705 in the icon representation 708. Within the designated analysis, the specific gate to be optimized is selected using one of the Graph buttons 710. Once an analysis and gate are specified, a graph 713 containing a FIG. 715 defining the gate boundary is displayed in the screen. In addition to the FIG. 715, the graph 713 also displays a plot of the input data from a well that is specified by activating an icon 718 in the multiplexed heat map 720. In the screen 700, a hatched pattern indicates that the icon representing sample position 718 corresponding to sample location E6 has been activated.

In order to optimize the gate boundaries, the user may adjust the size, shape and location of the FIG. 715 using the handles 722. Alternatively, the range of values represented in the region of the heat map representing the selected output data set may be adjusted using the Range box 725. Within the Range box 725, the maximum value and the minimum value for the visual display in the selected region may be specified by entering values in the maximum box 727 and the threshold box 730 or by positioning the sliders 733 and 735. The parameters in unit assignment box 740 may also be adjusted by a user interacting with the screen 700.

Advantageously, the visual representation of the output data in the heat map 720 may be updated in real time to reflect adjustments of the gate boundary, range, or units. This feature of the invention allows the user to rapidly evaluate the effects of analysis parameter optimization on the relationships in the displayed data and effectively utilize this knowledge during the optimization process.

Embodiments of the invention may be implemented on a wide range of conventional computer platforms including desktop and laptop personal computers. Implementations may be programmed using many different programming languages and the programming language used for implementation on a specific computer platform may be advantageously optimized for the specific platform. For example, the user interface of FIG. 14-FIG. 18 may be implemented on personal computers running the Leopard or Windows operating systems in $C^{++}$ using Qt, a development framework for cross platform application development from Trolltech of Oslo, Norway. The simultaneous display may be implemented as a grid view (the QTableView in the Qt framework, for example). Graphical rendering code draws each grid element according to the analysis result defined by protocol for the experiment.

Although the features of the present invention have been illustrated in an embodiment for the analysis of flow cytometry data, those skilled in the art of data analysis and display will realize that it may be used to analyze and compare location-specific data from a wide range of sources. These include but are not limited to the visual presentation of analyses of air, ground and water pollution levels at fixed geographic locations, analyses of process variables at specific locations within a manufacturing plant, analyses of agricultural parameters within a field, and other analyses in which the input data is obtained through the interrogation of samples in an arrangement of locations that may represented by an arrangement of icons in a user interface.

We claim:

1. A computer system comprising a processor, a display, and a graphical user interface for defining analyses of data sets resulting from cytometric interrogation of particle containing samples in a spatial arrangement of samples and visually representing results of the analyses on the display, where the visual representation enables identification of relationships among different data sets, the interface comprising:

a graphical presentation on the display of the computer system of an analysis that is applied to a data set to produce a set of results, the analysis having at least one parameter that a user controls by interacting with the graphical presentation, wherein the graphical presentation comprises a gate figure in a histogram or dot plot of the set of results, said gate figure defining a range or boundary for identifying events of interrogating and recording light pulses from particles in the sample, wherein a size, shape, or location of the gate figure is adjustable by the user and the interacting comprises adjusting the size, shape, or location of the gate figure;

a location-specific, multiplexed heat map on the display comprising a visual presentation of the set of results and at least one additional set of results, whereby the user determines the effects of adjusting the gate figure on the relationships among the data sets by viewing the heat map;

the heat comprising a spatial arrangement of icons similar to the spatial arrangement of the particle containing samples such that each of the icons is visually associated with one of the samples; and each of the icons is divided into at least a first region and a second region, the first region of the icon displaying information regarding a first analysis of a data set resulting from cytometric interrogation of a sample visually associated with the icon, and the second region of the icon displaying information regarding a second analysis of the data set resulting from cytometric interrogation of the sample visually associated with the icon.

2. The computer system of claim 1 wherein the samples are particle-containing biological samples.

3. The computer system of claim 1 wherein the samples are interrogated using one of a flow cytometer and a scanning cytometer.

4. The computer system of claim 1 wherein the visual presentation of the set of results tracks the changes in variable analysis parameter.

5. The computer system of claim 4 wherein the variable analysis parameter is changed by adjusting the shape of the gate figure in the graphical presentation.

6. The computer system of claim 5 wherein the gate figure and graphical presentation have one, two or three dimensions.

7. The computer system of claim 4 wherein the variable analysis parameter
is selected by activating buttons on a screen.

* * * * *

UNITED STATES PATENT AND TRADEMARK OFFICE
CERTIFICATE OF CORRECTION

PATENT NO. : 10,140,419 B2
APPLICATION NO. : 14/598878
DATED : November 27, 2018
INVENTOR(S) : Cappione, III et al.

Page 1 of 1

It is certified that error appears in the above-identified patent and that said Letters Patent is hereby corrected as shown below:

In the Claims

In Claim 1 at Column 14 Line 58, after "the heat" please insert --map--.

Signed and Sealed this
Fourth Day of June, 2019

Andrei Iancu
*Director of the United States Patent and Trademark Office*